(12) United States Patent
Armand

(10) Patent No.: US 6,288,187 B1
(45) Date of Patent: Sep. 11, 2001

(54) PERFLUOROVINYL IONIC COMPOUNDS AND THEIR USE IN CONDUCTIVE MATERIALS

(75) Inventor: Michel Armand, Montréal (CA)

(73) Assignees: ACEP Inc., Montreal (CA); Centre National de la Recherche Scientifique, Paris (FR); Université de Montréal, Montréal (CA)

( * ) Notice: Subject to any disclaimer, the term of this patent is extended or adjusted under 35 U.S.C. 154(b) by 0 days.

(21) Appl. No.: 09/269,268
(22) PCT Filed: Jul. 27, 1998
(86) PCT No.: PCT/FR98/01664
  § 371 Date: Mar. 25, 1999
  § 102(e) Date: Mar. 25, 1999
(87) PCT Pub. No.: WO99/05126
  PCT Pub. Date: Feb. 4, 1999

(30) Foreign Application Priority Data

Jul. 25, 1997 (CA) .................................................. 2212974

(51) Int. Cl.[7] .................. C07D 249/12; C07C 311/48; C07C 317/44; C08F 28/02; C08F 26/06
(52) U.S. Cl. .................. 526/240; 526/241; 526/242; 526/243; 526/247; 526/248; 526/251; 526/255; 526/258; 526/261
(58) Field of Search .................. 526/240, 241, 526/242, 243, 247, 248, 251, 255, 258, 261; 525/199, 200, 201, 202, 203, 212

(56) References Cited

U.S. PATENT DOCUMENTS 5,463,005  10/1995  Desmarteau .

FOREIGN PATENT DOCUMENTS 0 850 920 A2  7/1998  (EP) .
0 850 933 A1  7/1998  (EP) .
96/39379  12/1996  (WO) .

OTHER PUBLICATIONS

Desmarteu, Journal of Fluorine Chemistry, vol. 72, No. 2, Jun. 1995, pp. 203–208, XP002083040.
Database WPI, Section CH, Week 9308, XP002083041.

Primary Examiner—Nathan M. Nutter
(74) Attorney, Agent, or Firm—Burns, Doane, Swecker & Mathis, L.L.P.

(57) ABSTRACT

The invention relates to ionic compounds in which the negative charge is highly delocalized. The compounds comprise at least one perfluorovinyl group and at least one group chosen from —O or one of the groups —NC≡N, —C(C≡N)$_2$, —NSO$_2$R or —C[SO$_2$R]$_2$ or a pentacyclic group comprising at least one N, C—C≡N, CR, CCOR or CSO$_2$R group. The compounds and/or their polymers are of use in the preparation of ionically conducting materials, electrolytes and selective membranes.

11 Claims, No Drawings

PERFLUOROVINYL IONIC COMPOUNDS AND THEIR USE IN CONDUCTIVE MATERIALS

This application filed under 35 USC 371, claims benefit of priority from PCT/FR98/01664 filed Jul. 27, 1998.

BACKGROUND OF THE INVENTION

1. Field of the Invention

The subject matter of the present invention is ionic perfluorovinyl compounds, the polymers obtained from these compounds and their applications.

2. Description of the Prior Art

Polyelectrolytes of polyanion type incorporating functional groups of sulfonate or carboxylate type are known as ion-exchange resins (polyacrylic acid, polystyrenesulfonic acid optionally crosslinked with divinylbenzene). These polyelectrolytes are dissociated solely in the presence of water or of highly polar protic solvents, such as polyalcohols, for example ethylene glycol or glycerol. The corresponding acid groups (carboxylic or sulfonic acids) do not exhibit marked catalytic properties due to the absence of swelling of the resin and the strong association of ion pairs. In the form of membranes, these polymers only have a mediocre stability under the operating conditions of a hydrogen-air fuel cell; in particular, they are rapidly degraded by oxidizing species present on the oxygen electrode side. Likewise, these polymers cannot be used in membrane processes, such as the chlorine-sodium hydroxide electrochemical process.

Furthermore, perfluorinated membranes (Nafion®) carrying sulfonic groups are known which exhibit good chemical stability under the operating conditions of a fuel cell and for the chlorine-sodium hydroxide process. These materials are copolymers of tetrafluoroethylene (TFE) and of a comonomer carrying sulfonyl functional groups. However, the impossibility of crosslinking these polymers requires that the density of ionic groups be kept low, in order to prevent the resulting polymers from being excessively soluble or swollen by water, resulting in a mediocre mechanical strength and a relatively limited conductivity. Furthermore, these membranes exhibit a high permeability to gases (oxygen and hydrogen) and to certain solvents, such as methanol, which is harmful to the energy efficiency of fuel cells, more especially those of methanol-air type ("crossover"). Furthermore, although the sulfonate groups attached to perfluorinated groups are partially dissociated in aprotic solvents and although the solvating polymers are particularly advantageous for secondary batteries in which the reactions at the electrodes involve lithium ions, the conductivity of the gels obtained by swelling Nafion® membranes with aprotic solvents, alone or as a mixture, and the conductivity of the mixtures of these polyelectrolytes with polyethers based on ethylene oxide remain too low. Furthermore, the significant fraction of perfluorinated segments $-CF_2CF_2-$ resulting from the TFE comonomer makes these compounds sensitive to reduction at potentials close to those of the negative electrode, resulting in the polymer being destroyed. Moreover, the chemistry of these polymers is complex and expensive, and the yield in the manufacture of the monomer of perfluorovinyl ether type:

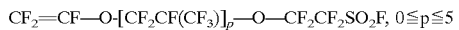

$$CF_2=CF-O-[CF_2CF(CF_3)]_p-O-CF_2CF_2SO_2F,\ 0\leq p\leq 5$$

by thermal cracking of perfluoropolyethers-acid fluoride obtained by addition of $CF_3CF=CF_2$ to isomerized sultones is low and limits the use of these materials.

Polymers which comprise anions attached to the backbone of the polymer and which are optionally plasticized or gelled by a solvent of polar type are of great advantage in electrochemical systems, such as primary or secondary batteries, supercapacitors or systems for modulating light (electrochromic windows). Such polymers are mainly derivatives of ethylene oxide, of acrylonitrile, of polyesters of alkyl or oxaalkyl acrylate or methacrylate type, or of vinylidene fluoride. The production of monomers carrying highly delocalized anionic functional groups which can be incorporated, either by copolymerization or by cocrosslinking or alternatively by mixing polymers, in macromolecular materials such as those used in the electrochemical systems described above is therefore highly advantageous. The ionic monomers described above as components of membranes of Nafion® type cannot be suitable for this use because the high fraction of perfluorinated segments necessary in order to obtain the maximum conductivity in aprotic media (# $1M.l^{-1}$) corresponds to a decreased dielectric constant in the vicinity of the ions and to an increased segmental stiffness, which are unfavorable to the movement of the ions. Moreover, the sulfonate groups are insufficiently dissociated in comparison with the salts of anions delocalized from nitrogenous centers or from carbon, such as, for example, the anion corresponding to the formula $(R_FSO_2)X(SO_2R'_F)^-$, in which X is N, C—R or C—$SO_2R''_F$, $R_F$, $R'_F$ and $R''_F$ are chosen from fluorine and fluorinated monovalent groups, or else $R_F$ and $R'_F$ form the components of a divalent ring, and R=H or any monovalent organic radical.

W. Navarrini et al. (U.S. Pat. No. 5,103,049) disclose methods for the preparation of $R_f$—CF=CF—$SO_2F$ compounds in which $R_f$ is F or a perfluoroalkyl group comprising 1 to 9 carbon atoms. Among these compounds, only $CF_2=CF-SO_2F$ is capable of acting as basis for monomers which can polymerize without steric constraints. However, this material has been shown to be too reactive to act as a precursor for monomer salts and anions, because the nucleophilic addition to the C=C double bond, which is depleted in electrons both by the fluorine atoms and by the $-SO_2F$ group, generally takes place more rapidly than the substitution of the fluorine of the $SO_2F$ group, thus preventing access to ionic monomers or to precursors of ionic compounds ("Studies of the Chemistry of Perfluorovinylsulfonyl Fluoride", Forohar Farhad, Clemson University, Thesis 1990 UMI 9115049). In particular, the methods for the preparation of anionic compounds used with $R_FSO_2F$ compounds cannot be applied to the compound $CF_2=CF-SO_2F$. A process which consists in attaching a perfluorovinyl group to a phenyl nucleus carrying an $SO_2F$ group has been provided by C. Stone et al. (WO/96/39379); however, in this case too, it is not possible to convert the $CF_2=CF-C_6H_4SO_2F$ molecule to an anionic monomer because of the sensitivity of the $CF_2=CF-$ group, which is more reactive than $-SO_2F$ with respect to bases of $OH^-$ or $NH_3$ type.

Another process for the preparation of monomers of the TFE type comprising an anion has been provided by D. Desmarteau et al. (U.S. Pat. No. 5,463,005). It consists in preparing a compound comprising a perfluorovinyl group and an $SO_2F$ group, in protecting the perfluorovinyl group, for example by addition of $Cl_2$, in converting the $SO_2F$ group to an ionic group and in then deprotecting the perfluorovinyl group. Such a process is nevertheless lengthy and expensive and the polymers obtained from said monomers exhibit the same disadvantages as the polymers of Nafion® type, resulting from the low content of $SO_3^-$ or sulfonimide ions in the absence of crosslinking.

The aim of the present invention is to provide a novel family of ionic compounds, which compounds exhibit extensive delocalization of the negative charge and good activity in polymerization or in copolymerization and allow the preparation of macromolecules possessing dissociated and stable ionic functional groups, and a process for the preparation of these compounds from fluorinated derivatives which are commercially available at low cost, for example hydrofluorocarbons or halocarbons.

For this reason, the subject matter of the present invention is ionic monomer compounds, the homopolymers and the copolymers obtained from these compounds, their applications and a process for their preparation.

SUMMARY OF THE INVENTION

A compound according to the invention is an ionic compound in which the negative charge is highly delocalized and which corresponds to the formula $[CF_2=CF-A^-]_m M^{m+}$, in which:

$M^{m+}$ is a proton or a metal cation having the valency m chosen from the ions of alkali metals, of alkaline earth metals, of transition metals or of rare earth metals or an organic onium cation or an organometallic cation, $1 \leq m \leq 3$;

$A^-$ represents an anionic group corresponding to one of the following formulae:

$[-(CF_2)_n-SO_2Z]^-$ (I)

$[-(O)_{n'}-\Phi-SO_2Z]^-$ (II)

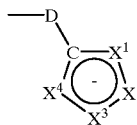 (III)

n and n' represent 0 or 1;

Φ represents a condensed or noncondensed aromatic group, which may or may not carry one or more substituents and which may or may not comprise heteroatoms, or a polyhalogenated group $-C_6H_{(4-x-y)}F_xCl_y-$ ($1 \leq x+y \leq 4$);

Z represents —O or one of the $-NC\equiv N$, $-C(C\equiv N)_2$, $-NSO_2R$ or $-C[SO_2R]_2$ groups, Z being other than —O when n or n' are zero;

D represents a single bond, an oxygen atom, a sulfur atom, a —CO— carbonyl group or an —SO$_2$— sulfonyl group;

the groups $X^1$ to $X^4$, hereinafter denoted by $X^i$, represent N, C—C≡N, CR, CCOR or CSO$_2$R, it being understood that, in a pentacyclic group, the xi groups can be identical or different;

R represents Y, YO—, YS—, Y$_2$N—, F, $R_F=C_qF_{2q+1}$ (preferably $0 \leq q \leq 12$), $CF_2=CF-$, $CF_2=CFCF_2-$ or $CF_2=CF-O-$, it being understood that, if 2 R substituents are present on the same group, they can be identical or different;

Y represents H or a monovalent organic radical having from 1 to 16 carbon atoms chosen from alkyl, alkenyl, oxaalkyl, oxaalkenyl, azaalkyl, azaalkenyl, aryl or alkylaryl radicals or from the radicals obtained from the abovementioned radicals by substitution, in the chains and/or the aromatic part, by heteroatoms, such as halogens, oxygen, nitrogen, sulfur or phosphorus, it being understood that if sulfur or phosphorus are present, they can optionally be bonded to substituted nitrogen or oxygen atoms, or else Y is a repeat unit of a polymeric backbone.

The divalent radical Φ can be a phenyl $C_6H_4$ corresponding to the ortho, meta and para positions of substitution. It can be an aromatic group, a phenyl which is substituted and/or comprising condensed nuclei which may or may not comprise heteroatoms. Φ is preferably a halogenated phenyl group or a phenyl group carrying 1 to 2 $CF_3$ substituents or a pyridyl nucleus.

When $M^{m+}$ is a metal cation, it can be an alkali metal (in particular $K^+$ or $Li^+$), an alkaline earth metal (in particular $Mg^{++}$, $Ca^{++}$ or $Ba^{++}$), a transition metal (in particular $Cu^{++}$, $Zn^{++}$ or $Fe^{++}$) or a rare earth metal (in particular $Re^{+++}$).

When $M^{m+}$ is an onium cation, it can be chosen from ammonium ions $[N(Y^j)_4]^+$, amidinium ions $RC[N(Y^j)_2]^+$, guanidinium ions $C[N(Y^j)_2]_3^+$, pyridinium ions $[C_5N(Y^j)_6]^+$, imidazolium ions $C_3N_2(Y^j)_5^+$, imidazolinium ions $C_3N_2(Y^j)_7^+$, triazolium ions $C_2N_3(Y^j)_4^+$, carbonium ions $C_5(Y^j)_5C^+$, $NO^+$ (nitrosyl) or $NO_2^+$ ions, sulfonium ions $[S(Y^j)_3]^+$, phosphonium ions $[P(Y^j)_4]^+$ and iodonium ions $[I(Y^j)_2]^+$. In the various abovementioned onium ions, the $Y^j$ substituents of the same cation can be identical or different. They represent one of the substituents indicated above for Y.

When $M^{m+}$ is an organometallic cation, it can be chosen from metalloceniums. It can also be chosen from metal cations coordinated by atoms, such as O, S, Se, N, P or As, carried by organic molecules, these cations optionally forming part of a polymeric backbone. $M^{m+}$ can also be a cation derived from the alkyl groups defined for Y above and limited to those having from 1 to 10 carbon atoms, for example a trialkylsilyl, trialkylgermany or dialkylstannyl derivative; in this case, M is connected to $[CF_2=CF-A]$ by a very labile covalent bond and the compound behaves as a salt. The $M^{m+}$ cation can also be the repeat unit of a conjugated polymer in cationic oxidized form.

DETAILED DESCRIPTION OF THE PREFERRED EMBODIMENTS

Mention may be made, among the compounds of the present invention, of the following monofunctional monomers:

$\{[CF_2=CF-SO_2NCN]^-\}_m M^{m+}$,
$\{[CF_2=CF-SO_2C(CN)_2]^-\}_m M^{m+}$, $\{[CF_2=CFCF_2-SO_2NCN]^-\}_m M^{m+}$,
$\{[CF_2=CFCF_2-SO_2C(CN)_2]^-\}_m M^{m+}$, $\{[CF_2=CF-\Phi SO_2NCN]^-\}_m M^{m+}$, $\{[CF_2=CF-\Phi SO_2C(CN)_2]^-\}_m M^{m+}$, $\{[CF_2=CF-\Phi SO_2NSO_2CF_3]^-\}_m M^{m+}$,
$\{[CF_2=CF-\Phi SO_2C(SO_2CF_3)_2]^-\}_m M^{m+}$, $\{[CF_2=CF-\Phi SO_2CH(SO_2CF_3)]^-\}_m M^{m+}$,

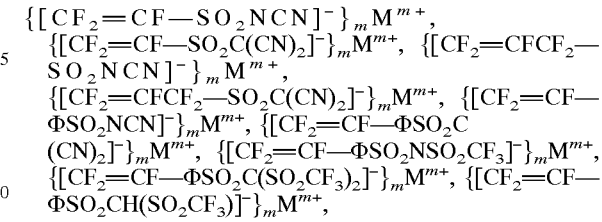

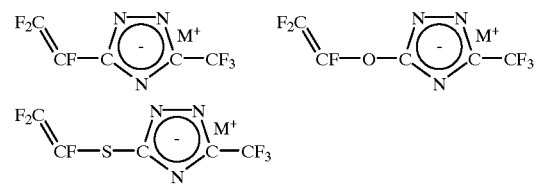

Mention may also be made of the following di- and trifunctional monomers
$\{[(CF_2=CFCF_2-SO_2)_2N]^-\}_m M^{m+}$,
$\{[(CF_2=CFSO_2)_2CH]^-\}_m M^{m+}$,
$\{[(CF_2=CFCF_2-SO_2)_2CH]^-\}_m M^{m+}$,
$\{[(CF_2=CF-SO_2)_3C]^-\}_m M^{m+}$,
$\{[(CF_2=CFCF_2-SO_2)_3C]^-\}_m M^{m+}$, $\{[(CF_2=CF-\Phi SO_2)_2N]^-\}_m M^{m+}$, $\{[(CF_2=CF-O-\Phi SO_2)_2N]^-\}_m M^{m+}$, $\{[(CF_2=CF-\Phi SO_2)_2CH]^-\}_m M^{m+}$,
$\{[(CF_2=CF-O-\Phi SO_2)_2CH]^-\}_m M^{m+}$, $\{[(CF_2=CF-\Phi SO_2)_3C]^-\}_m M^{m+}$,
$\{[(CF_2=CF-O-\Phi SO_2)_2CH]^-\}_m M^{m+}$,
$\{[(CF_2=CF-\Phi SO_2)_3C]^-\}_m M^{m+}$, $\{[(CF_2=CF-O-\Phi SO_2)_3C]^-\}_m M^{m+}$, $\{[(CF_2=CF-)_2C_6H_3SO_3]^-\}_m M^{m+}$,
$\{[3,5-(CF_2=CF-)_2C_6H_3SO_2NSO_2CF_3]^-\}M^{m+}$

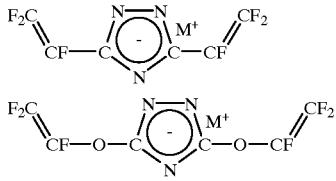

Preference is very particularly given, among the above-mentioned compounds, to those in which $\Phi$ is $-C_6H_4-$.

The ionic monomer compounds of the present invention can be prepared by various synthetic routes.

In a first embodiment, a compound comprising the perfluorovinyl group is reacted with an ionic compound having an anionic part $A^1$, the structure of which is analogous to that of the anionic part A of the desired compound, and having from one to 3 leaving groups.

The subject matter of the invention is a process for the preparation of an ionic monomer compound $[CF_2=CF-A^-]_m M^{m+}$ as defined above in which an organometallic compound (OM1) is reacted in stoichiometric proportions with an ionic compound (IC1) in the presence of a catalyst, characterized in that:

the organometallic compound (OM1) corresponds to the formula $(CF_2=CF-(CF_2)_n\cdot_e-E$, in which:

E represents Li, $MgL^1$, $ZnL^1$, $CdL^1$, Cu, Mg, Zn, Cd, Hg or a trialkylsilyl, trialkylgermanyl or trialkylstannyl group;

n is 0 or 1;

represents the valency of E;

$L^1$ represents a leaving group chosen from halogens, pseudohalogens, including sulfonates, radicals comprising imidazole or 1,2,4-triazole rings and their homologs in which one or more carbon atoms carry substituents, including those in which the substituents form a ring (for example a benzotriazole), perfluoroalkylsulfonyloxy radicals and arylsulfonyloxy radicals;

the ionic compound (IC1) corresponds to the formula $[(LA^1)^-]_m M'^{m+}$ in which:

$M'^{m+}$ represents a proton or a metal cation having the valency m chosen from ions of alkali metals, of alkaline earth metals, of transition metals or of rare earth metals, or an organic onium cation, or an organometallic cation, $1 \leq m \leq 3$. M' is chosen so as not to interfere with the formation reaction;

L has the same meaning as $L^1$, it being understood that the L and $L^1$ groups of the respective reactants used during a reaction can be identical or different;

$A^1$ represents an anionic group corresponding to one of the following formulae:

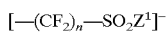

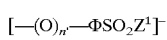

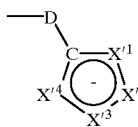

in which:

n and n' represent 0 or 1;

D represents a single bond, an oxygen atom, a sulfur atom, a $-CO-$ carbonyl group or an $-SO_2-$ sulfonyl group;

$Z^1$ represents the $-O$ oxygen (except if n or n' are zero) or one of the $-NC\equiv N$, $-C(C\equiv N)_2$, $-NSO_2R^1$ and $-C[SO_2R^1]_2$ groups;

the $X'^1$ to $X'^4$ groups, hereinafter denoted by $X'^i$, represent N, $C-C\equiv N$, $CR^1$, $CCOR^1$ or $CSO_2R^1$, it being understood that, in a pentacyclic group, the $X'^i$ groups can be identical or different;

$R^1$ represents Y, YO—, YS—, $Y_2N$—, F, $CF_2=CF-$, $CF_2=CFCF_2-$, $CF_2=CF-O-$ or $R_F=C_qF_{2q+1}$ ($0 \leq q \leq 12$), or a leaving group chosen from halogens, pseudohalogens, including sulfonates, radicals comprising imidazole or 1,2,4-triazole rings and their homologs, perfluoroalkylsulfonyloxy radicals and arylsulfonyloxy radicals, it being understood that, if two $R^1$ substituents are present on the same group, they can be identical or different and that at most two $R^1$ substituents are leaving groups;

Y has the meaning given above.

When the M' cation of the reactant used is different from the M cation of the desired final compound, the compound obtained is modified by conventional cation-exchange techniques.

The preferred leaving groups L and $L^1$ are F, Cl, Br, I, the imidazole radical, the trifluoromethanesulfonyloxy radical $CF_3SO_3-$ and arylsulfonyloxy radicals.

Preference is very particularly given, for the ionic compounds (IC1), to the following anionic groups: $[(FSO_2)NSO_2R_F]^-$, $[(ClSO_2)NSO_2R_F]^-$, $[(ImSO_2)NSO_2R_F]^-$, $[(FSO_2)_2N]^-$, $[(ClSO_2)_2N]^-$, $[(ImSO_2)_2N]^-$, $[(FSO_2)NCN]^-$, $[(ClSO_2)NCN]^-$, $[(ImSO_2)NCN]^-$, $[(FSO_2)C(R)SO_2R_F]^-$ $[(ClSO_2)C(R)SO_2R_F]^-$, $[(ImSO_2)C(R)SO_2R_F]^-$, $[(FSO_2)_2CR]^-$, $[(ClSO_2)_2CR^-$, $[(ImSO_2)_2CR]^-$, $[(FSO_2)C(CN)_2]^-$, $[(ClSO_2)C(CN)_2]^-$, $[(ImSO_2)C(CN)_2]^-$, $(FSO_2)_3C]^-$, $[(ClSO_2)_3C]^-$, $[(ImSO_2)_3C]^-$, $[(Cl\Phi SO_2)NSO_2R_F]^-$, $[(Br\Phi SO_2)NSO_2R_F]^-$, $[(I\Phi SO_2)NSO_2R_F]^-$, $[(CF_3SO_3\Phi SO_2)NSO_2R_F]^-$, $[(CH_3\Phi SO_3\Phi SO_2)NSO_2R_F]^-$, $[3,5-Br_2C_6H_3SO_3]^-$, $[3,5-Br_2C_6H_3SO_2R)]^-$, $[(3,5-I_2C_6H_3SO_3]^-$, $[3,5-I_2C_6H_3SO_2N(SO_2R_F)]^-$, $[(Br\Phi SO_2)NCN^-$, $[(I\Phi SO_2)NCN]^-$, $[(CF_3SO_3\Phi SO_2)NCN]^-$, $(CH_3\Phi SO_3\Phi SO_2)NCN]^-$, $[(CH_3\Phi SO_2)C(CN)_2]^-$, $[(Br\Phi SO_2)C(CN)_2]$, $[(I\Phi SO_2)C(CN)_2]^-$, $[(CF_3SO_3\Phi SO_2)C(CN)_2]^-$, $[(CH_3\Phi SO_3\Phi SO_2)(CN)_2]^-$, $[(Cl\Phi SO_2)N(SO_2\Phi Cl)]^-$, $[(Br\Phi SO_2)N(SO_2\Phi Br)]^-$, $[(I\Phi SO_2)N(SO_2\Phi)]^-$, $[(CF_3SO_3\Phi SO_2)N(SO_2\Phi SO_3CF_3)]^-$, $[(CH_3\Phi SO_3\Phi SO_2)N(SO_2\Phi SO_3\Phi CH_3)]^-[(Cl\Phi SO_2)_2C(SO_2R_F)]^-$, $[(Br\Phi SO_2)_2C(SO_2R_F)]^-$, $[(I\Phi SO_2)_2C(SO_2R_F)]^-$, $[(CF_3SO_3\Phi SO_2)_2C(SO_2R_F)]^-$, $[(Cl\Phi SO_2)C(SO_2R_{F2})_2]^-$, $[(Br\Phi SO_2)C(SO_2R_{F2})_2]^-$, $[(I\Phi SO_2)C(SO_2R_{F2})_2]^-$, $[(CF_3SO_3\Phi SO_2)C(SO_2R_{F2})_2]^-$, $[(CH_3\Phi SO_3\Phi SO_2)C(SO_2R_{F2})_2]^-$, $[Br\Phi C(SO_2R_{F2})^-$, $[3,5-Br_2C_6H_3C(SO_2R_F)_2]^-$,

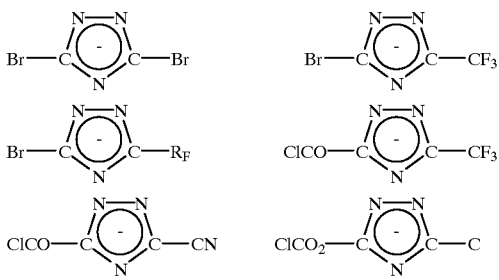

In the abovementioned anionic groups of the compounds (IC1), R and $R_F$ have the meaning given above and preferably comprise from 0 to 10 carbon atoms.

A compound (OM1) such as $CF_2=CF—Li$ is prepared by reaction of a strong base B and of a lithiating agent R'—Li with 1,1,1,2-tetrafluoroethane at low temperature, according to the reaction scheme:

$$CF_2—CH_2F+B \rightarrow CF_2=CHF+[BHF]$$

$$CF_2=CHF+R'Li \rightarrow CF_2=CFLi+LiF+R'H$$

The compounds $CF_2=CF—E$ in which E is other than Li can be obtained by ion exchange.

It is advantageous to use butyllithium both as strong base and as lithiating agent.

The compound $CF_2=CFCF_2—E$ can be prepared from perfluoroallyl fluorosulfate by simple nucleophilic substitution according to the following reaction scheme:

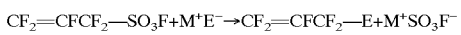

KI is a particularly appropriate compound $M^+E^-$.

The organometallic compounds (OM1) are more particularly chosen from: $CF_2=CFLi$, $(CF_2=CF)_{2-x}Mg(Hal)_x$, $(CF_2=CF)_{2-x}Zn(Hal)_x$, $(CF_2=CR)_{2-x}Cd(Hal)_x$ ($0 \leq x \leq 2$); Hal=Cl, Br, I, pseudohalogen), $(CF_2=CF)_{3-y}Al(Hal)_y$, ($0 \leq y < 3$); $CF_2=CFCu$, $CF_2=CFSi(CH_3)_3$, $CF_2=CFSi(C_2H_5)_3$, $CF_2=CFSn(CH_3)_3$, $CF_2=CFSn(C_2H_5)_3$, $CF_2=CFSn(C_4H_9)_3$, $CF_2=CFCF_2CdBr$, $CF_2=CFCF_2Cu$, $CF_2=CFCF_2Zn(O_3SF)$, $CF_2=CFCF_2Si(CH_3)_3$ and $CF_2=CFCF_2Si(C_2H_5)_3$.

It is known to a person skilled in the art that the stability and the processing conditions for halogenated organometallic compounds vary according to the nature of E; in particular, organolithium compounds are only stable at temperatures of less than −60° C. and are habitually prepared and used at the temperature of dry ice, whereas more covalent compounds, such as silane derivatives, are stable even above room temperature.

The process is carried out in the presence of a catalyst chosen from derivatives of nickel or palladium coordinated with bases of amine or phosphine type. Mention may be made, by way of example, of nickel bis(2,2'-bipyridyl), nickel tetrakis(triphenylphosphine) and its sulfonated derivatives, palladium acetate, trisbenzylideneketonedipalladium, palladium tetrakis(triphenylphosphine) and its sulfonated derivatives, and the compounds obtained by replacement of two triphenylphosphine molecules by $[(C_6H_5)_2PCH_2]_2$ or $[(C_6H_5)_2PCH_2]_2CH_2$. Nickel and palladium have catalytic properties for so-called Suzuki coupling reactions when their degree of oxidation is greater than or equal to 0 and less than or equal to 2.

In another embodiment of the invention, an ionic monomer compound $[CF_2=CF—A^-]_mM^{m+}$ according to the invention is prepared by reacting a compound comprising a protected fluorovinyl group $CF_2L^3CFL^4—(CF_2)_nE^1$ with a reactant $[(L^5)_aA^2]_{m'}M^{'m'+}$ making possible the formation of the anionic group A and then the protective groups are removed by a chemical or electrochemical reduction or by a dehydrohalogenation. M' has the meaning indicated above. $L^3$ and $L^4$ represent H or a halogen, just one among them optionally being H. $E^1$ has the meaning given above for E. $L^5$ represents a leaving group having the same definition as the leaving group L. "a" is the valency of the anionic group $A^2$. $A^2$ represents a group corresponding to one of the following formulae $[—(CF_2)_n—SO_2Z^2]^-$, $[—(O)_{n'}—\Phi SO_2Z^2]^-$ or

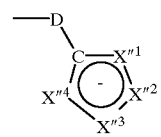

in which:

n, n', D and $\Phi$ have the meaning indicated above;

$Z^2$ represents the —O oxygen (except if n or n' are zero) or one of the groups $—NC\equiv N$, $—C(C\equiv EN)_2$, $—NSO_2R^2$ or $—C[SO_2R^2]_2$; the groups $X^{"1}$ to $X^{"4}$, hereinafter denoted by $X^{"i}$, represent N, $C—C\equiv N$, $CR^2$, $CCOR^2$ or $CSO_2R^2$, it being understood that, in a pentacyclic group, the $X^{"i}$ groups can be identical or different;

$R^2$ represents OH, —SH, Y, YO—, YS—, $Y_2N—$, F, $CF_2=CF—$, $CF_2=CFCF_2—CF=CF—O—$ or $R_F=C_qF_{2q+1}$ ($0 \leq q \leq 12$), it being understood that, if two $R^2$ substituents are present on the same group, they can be identical or different and that at most two R substituents represent —OH or —SH;

Y has the meaning given above.

Mention may be made, by way of example, of the following reaction:

$$(ClSO_2)_2NK+2CF_2Cl—CFClLi \rightarrow (CF_2Cl—CFClSO_2)_2NK+2LiCl.$$

When the cation M' of the reactant used is different from the cation M of the desired final compound, the compound obtained is modified by conventional cation-exchange techniques. The greater resistance of the compounds thus protected with respect to nucleophiles, in particular bases, makes it possible to carry out reactions on molecules acting as intermediate in the preparation of the monomer anions, reactions which would be impossible if the ethylenic double bond was unprotected. In particular, it is possible to form intermediates of sulfamide or hydrazide type allowing the construction of anionic species.

For example, the anion derived by addition of chlorine to trifluoroacrylic acid can be converted to a triazole group via a hydrazide. The triazole anion, more dissociated than the carboxyl anion, is obtained according to the simplified scheme:

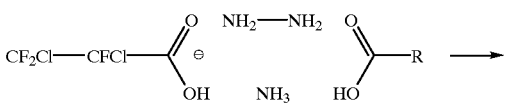

-continued $$CF_2Cl—CFCl—\underset{N}{\underset{\|}{\overset{N==N}{\overset{\|}{\bigcirc}}}}—R + 4H_2O$$

The starting fluorinated acrylic acid is easily prepared by reaction of $CO_2$ with an organometallic derivative, such as $CF_2$=CFLi, itself easily obtained by reaction of an alkyl-lithium with the commercial compound 1,1,1,2-tetrafluoroethane sold under the tradename Klea®.

Similar reactions are possible with a compound comprising a sulfur-based anionic group, such as a sulfonate. They make it possible to obtain, via a sulfamide, a compound comprising an anionic sulfonylimide group which is more dissociated than the sulfonate group, by the following reaction stages:

sulfonate+chlorinating agent→$RSO_2Cl$ $RSO_2Cl+NH_3→RSO_2NH_2$;

$RSO_2NH_2+R'SO_2Cl→RSO_2N(H)SO_2R'$

These reactions cannot be carried out if R=$CF_2$=CF. On the other hand, the desired result is obtained if R=$CF_2Cl$—CFCl and, for example, R'=R or $CF_3$. The sulfonate is easily obtained by the following reactions:

$CF_2Cl—CFClLi+ClSO_3Si(CH_3)_3→CF_2Cl—CFSO_3Li+ClSi(CH_3)_3$.

A compound $[CF_2L^2—CFL^3—(CF_2)_n]—E^1$, in particular $CF_2ClCFClLi$, can be obtained by reaction of the corresponding compound $[CF_2=CF—(CF_2)_n]—E^1$ with a compound $L^2L^3$ at a temperature of between −80° C. and 110° C., for example in the Trapp mixture (THF/ether pentane composition). Mention may be made, among the compounds $L^2L^3$ which are easily added to the perfluorovinyl double bond, of FCl, $Cl_2$, ClBr, $Br_2$, ICl, IBr, $I_2$, $(SCN)_2$, HCl, HBr and HI. The lithium compounds (OM2) can act as the basis for the preparation of other organometallic compounds, such as silicon or zinc derivatives, by exchange.

The $(L^2)/(L^3)$ and $L^2H$ pairs are preferably chosen from $Cl_2$, $Br_2$, FCl, FBr, BrCl, ICl, HF, HCl and HBr, $Cl_2$ and HCl being particularly preferred.

The $L^2L^3$ groups are easily removed by reduction or by dehydrohalogenation. The reducing agent is advantageously chosen from zinc, the copper-zinc couple, $Ti^{3+}$, $V^{2+}$, $Cr^{3+}$ or $Sm^{2+}$ salts, and tetrakis(dimethylaminoethylene) $\{[(CH_3)_2N]_2C=\}_2$. An electrochemical reduction can also be carried out, directly or via the preceding metals acting as mediators. The dehydrohalogenating agents are chosen from strong bases and are known to a person skilled in the art. Mention may in particular be made of NaH [optionally used in the presence of phosphorus-comprising bases of phosphazene P1–P4 type (Fluka AG, Basle, Catalog No. 79408, 79412, 79417, 79421, 422 79432)], $(CH_3)_3CONa$, $(CH_3)_3COK$, LDA (lithium diisopropylamide), $[(CH_3)_2CH]_2NLi$, or hexaalkyldisilazane derivatives, in particular $[(CH_3)_3Si]_2NLi$, $[(CH_3)_3Si]_2NNa$ and $[(CH_3)_3Si]_2NK$.

In another embodiment, an ionic compound having an anionic part $A^3$, the structure of which is analogous to that of the anionic part A of the desired compound, and having from one to 3 hydroxyl or thiol groups is reacted with a compound comprising the perfluorovinyl group.

The subject matter of the invention is a process for the preparation of an ionic monomer compound $[CF_2=CF—A^-]_mM^{m+}$ as defined above, characterized in that a compound $CF_2=CFL^2$, in which $L^2$ represents Cl, Br or F, is reacted in stoichiometric proportions with an ionic compound (IC2) $[(HQA^3)^-]_m(M')^{m+}$ and in that the addition product obtained is treated with a strong base B.

The reaction scheme is as follows:

$CF_2=CFL^2+(HQA^3)^-→HCF_2—CFL^2—Q—A^3$ $HCF_2—CFL^2—Q—A^3+Base →CF_2=CF—Q—A^3+BaseHI$ The cationic part $(M')^{m'+}$ has the meaning given above, alkali metal cations being preferred.

The anionic part $(HQA^3)^-$ is such that:

Q represents O or S;

$A^3$ represents an anionic group corresponding to one of the following formulae:

$$\underset{X'''3}{\overset{}{X'''4\diagdown\underset{}{\overset{C}{\bigcirc}}\diagup X'''2}}$$

in which:

n and Φ have the meaning indicated above;

$Z^3$ represents the —O oxygen (except if n is zero) or one of the groups —NC≡N, —C(C≡N)$_2$, —$NSO_2R^3$ or —$C[SO_2R^3]_2$;

the groups $X'''^1$ to $X'''^4$, hereinafter denoted by $X'''^i$, represent N, C—C≡N, $CR^3$, $CCOR^3$ or $CSO_2R^3$, it being understood that, in a pentacyclic group, the $X'''^i$ groups can be identical or different;

$R^3$ represents HO—, HS—, Y, YO—, YS—, $Y_2N$—, F, $CF_2$=CF—, $CF_2$=$CFCF_2$—, $CF_2$=CF—O— or $R_F$=$C_qF_{2q+1}$ (0≦q≦12), it being understood that, if two $R^3$ substituents are present on the same group, they can be identical or different and that at most two $R^3$ substituents are —OH or —SH groups;

Y is as defined above.

The strong base B can be in particular NaH [optionally used in the presence of phosphorus-comprising bases of phosphazene P1–P4 type (Fluka A G, Basle, Catalog No. 79408, 79412, 79417, 79421, 422 79432)], $(CH_3)_3CONa$, $(CH_3)_3COK$, LDA (lithium diisopropylamide), $[(CH_3)_2CH]_2NLi$, or hexaalkyldisilazane derivatives, in particular $[(CH_3)_3Si]_2NLi$, $[(CH_3)_3Si]_2NNa$ and $[(CH_3)_3Si]_2NK$. Potassium t-butoxide is particularly appropriate.

When the ionic compound (IC2) comprises a thiol, it is possible to convert the sulfide of the anion $[HCF_2—CFL^2SA]^-$ of the intermediate product obtained to the sulfone by oxidation. The electro-withdrawing power of the sulfone contributes to decreasing the basicity of the corresponding anion $[HCF_2—CFL^2—SO_2—A]^-$ and it is then possible to remove $L^2H$ under mild conditions, for example in the presence of a tertiary nitrogenous base. The preferred compounds (IC2) are those which comprise one of the following anions:

$[\{HO—(\Phi)SO_2\}N(SO_2R_F)]^-$, $[\{HS—(\Phi)SO_2\}N(SO_2R_F)]^-$, $[\{HO(\Phi)SO_2\}NCN]^-$, $[\{HS(\Phi)SO_2\}NCN]^-$, $[\{HO(\Phi)SO_2\}C(CN)_2]^-$, $[\{HS(\Phi)SO_2\}C(CN)_2]^-$, $[\{HO(\Phi)SO_2\}N\{SO_2(\Phi)OH\}]^-$, $[\{HS(\Phi)SO_2\}N(\Phi)SH]^-$, $[\{HO(\Phi)SO_2\}_2C(R)]^-$, $[\{HO(\Phi)SO_2\}_2C(SO_2R)]^-$, $[\{HO(\Phi)SO_2\}_2C(SO_2R_F)]^-$, $[\{HO(\Phi)SO_2\}C(SO_2R_F)_2]^-$, $[\{HS(\Phi)SO_2\}_2C(R)]^-$, $[\{HS(\Phi)SO_2\}_2C(SO_2R)]^-$, $[\{HS(\Phi)SO_2\}_2C(SO_2R_F)]^-$, $[\{HS(\Phi)SO_2\}C(SO_2R_F)_2]^-$, $[3,5-(HO)_2—C_6H_3C(SO_2R_F)]^-$, $[(3,5-(HO)_2—C_6H_3SO_2)N(SO_2R_F)]^-$, $[3,5-(HO)_2—C_6H_3C(SO_2R_F)]^-$, $[\{HO—(\Phi)SO_2\}_2C(SO_2R_F)]^-$, $[\{HS—(\Phi)SO_2\}_2C(SO_2R_F)]^-$,

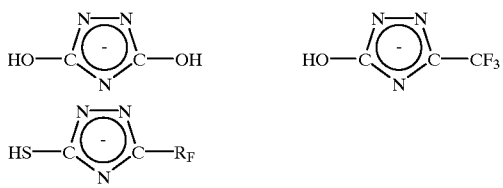

In another embodiment, the compounds $[CF_2=CF-A^-]_m M^{m+}$ are prepared by a process, characterized in that it consists in reacting a compound $L^6CF_2CF_2L^6$ with an ionic compound $[(HQA^3)^-]_{m'}(M')^{m'+}$ in stoichiometric proportions and in reducing the substitution compound obtained, either chemically or electrochemically. The compound $[(HQA^3)^-]_{m'}(M')^{m'+}$ is as defined above. $L^6$ represents a leaving group chosen from halogens, pseudohalogens and sulfonates. Halogens are particularly preferred.

The substitution compounds obtained are subjected to a chemical reduction or an electrochemical reduction in order to remove the $L^6$ leaving groups. The reduction can be catalyzed by zinc, the copper-zinc couple, $Ti^{3+}$, $V^{2+}$, $Cr^{3+}$ or $Sm^{2+}$ salts, and tetrakis(dimethylaminoethylene) $\{[(CH_3)_2N]_2C=\}_2$. An electrochemical reduction can be carried out, directly or via the preceding metals acting as mediators.

The ionic compounds of the present invention, all of which comprise at least one $CF_2=CF-$ group, can be polymerized by the radical route. The polymerization can be carried out in solution or in emulsion with conventional radical initiators, such as peroxides, azo compounds, persulfates, photoinitiators of benzoin type or others. During the preparation of crosslinked materials, the molecular mass between network nodes is not necessarily very high, which constitutes a significant advantage with respect to materials of the Nafion type.

A polymer according to the present invention is composed of a polyanionic part with which are associated cations in a number sufficient to ensure the electronic neutrality of the polymer, the polyanionic part being composed of repeat units:

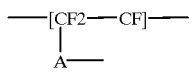

in which A has the meaning given above in the definition of the monomer compounds of the present invention.

A polymer of the invention can also be composed of repeat units

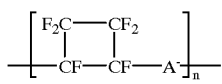

Such a polymer is obtained by polymerization of a difunctional compound according to the invention in which the anionic group A itself comprises a perfluorovinyl radical.

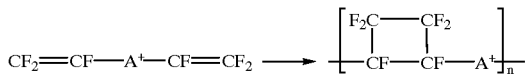

Such a compound $[(CF_2=CF)_2-A'^-]_m M^{m+}$ in which M has the meaning given above and A' represents an anion corresponding to one of the formulae (I), (II) or (III) mentioned above in which a Z or $X^i$ substituent comprises a perfluorovinyl radical. In this case, two perfluorovinyl radicals form a ring comprising 4 carbons which is connected to an analogous ring via the anionic part A' in order to form a linear polymer.

The polymerization can be carried out starting from only the compounds of the invention and a homopolymer is obtained in which each of the repeat units carries an ionic group.

When the polymerization is carried out in the presence of a comonomer, it is possible to limit the amount of ionic groups on the copolymer.

The polymerization of monofunctional monomers makes it possible to obtain linear polymers. The polymerization of di- or trifunctional monomers, in which the anionic group A itself comprises one or two additional $CF_2=CF-$ groups, makes it possible to obtain crosslinked macromolecular materials. In this case also, a copolymerization with a comonomer not carrying ionic groups makes it possible to adjust the number of functional groups introduced.

Generally, when the compounds of the present invention are polymerized in the presence of a comonomer, the choice of the monomer, of the comonomer and of the number of polymerizable groups on the monomer and the comonomer makes it possible to adjust the properties of the macromolecular materials obtained according to the use which is anticipated for them.

The ionic compounds of the present invention comprise at least one ionophoric group. They can thus be used for the preparation of ion conducting materials. The polymers obtained from the monomer compounds of the invention, which have the property of polymerizing or of copolymerizing, comprise repeat units carrying an ionophoric group and can thus also be used for the preparation of ion conducting materials, with the advantage of having an immobile anionic charge. An ion conducting material constituted by an ionic monomer compound in solution in a solvent and an ion conducting material comprising a polymer obtained by polymerization of a monomer compound of the present invention consequently constitute further subject matters of the present invention.

The ion conducting materials of the present invention can be used for the preparation of the electrolyte or as binder of the electrodes of energy storage systems, such as primary or secondary batteries, fuel cells, in supercapacitors, in systems for modulating light transmission (electrochromic systems, electroluminescent diodes) or in sensors. An electrolyte obtained from a compound according to the invention can be a liquid electrolyte, a solid electrolyte or a gel electrolyte.

A plasticized electrolyte or an electrolyte in the gel form according to the invention can be composed of a mixture of at least one polar solvent, of an ionic monomer compound of the invention and of a polar polymer. It can also be composed of at least one polar solvent and a polymer or copolymer obtained by polymerization of a monofunctional compound according to the present invention.

A solid electrolyte according to the invention comprises either a copolymer of at least one compound according to the invention and of one or more precursors of solvating polyethers or a macromolecular material obtained by co-crosslinking of at least one compound according to the invention and of a solvating polyether carrying reactive functional groups capable of reacting with the perfluorovinyl group of the compounds of the invention. In another embodiment, a solid electrolyte can comprise a mixture of a polyether and of a homopolymer or of a copolymer obtained from at least one compound of the invention carrying ionic groups, it being possible for said mixture optionally to be crosslinked in order to form an interpenetrating network. In some cases, it can be advantageous to plasticize the macromolecular material by addition of a polar solvent which is compatible with the ether functional groups. Depending on the amount of polar solvent added, the electrolyte will be a plasticized solid electrolyte or a gel electrolyte. The polar solvent is chosen, for example, from linear ethers and cyclic ethers, esters, nitrites, nitro derivatives, amides, sulfones, alkylsulfamides and partially halogenated hydrocarbons.

An electrolyte can also be composed of a mixture of a homopolymer or of a copolymer of polar monomers (including a polyether) and of a homopolymer or of a copolymer of ionic compounds of the present invention. The two mixed polymers can optionally be crosslinked to form an interpenetrating network and be plasticized by a polar liquid.

An electrolyte generally comprises a solvent (liquid, solid or gel) and at least one salt. When, in accordance with the present invention, an electrolyte comprises a macromolecular material obtained from the compounds of the invention, the repeat units comprise ionic groups which can completely or partially replace the salt conventionally added to a polymer solvent in order to constitute a polymer electrolyte. Polymers derived from trifluorovinylsulfonyl (trifluoromethylsulfonyl)imide and those derived from trifluorovinylphenylsulfonyl(trifluoromethylsulfonyl)imide are particularly advantageous for the preparation of electrolytes. An electrolyte obtained from a polymer according to the invention, in which the anions are at least partly immobilized on a polymer chain, has a mainly cationic mobility, the effect of which is to greatly improve the operation of electrochemical systems. In addition, a compound of the invention can be used as salt added to a liquid or polymer electrolyte.

Use is preferably made, for the preparation of macromolecular materials of use as electrolyte, of compounds according to the invention in which the cation is an alkali metal cation. Lithium and potassium are particularly preferred. The more suitable anions are the mono- or difunctional imides $CF_2=CFSO_2NSO_2CF_3^-$ or $[CF_2=CFSO_2]_2N^-$ or $CF_2=CFC_6H_4SO_2NSO_2CF_3^-$.

When an electrolyte according to the present invention is used in an energy storage system, such as a primary battery or a secondary battery, it is advantageous to use, as negative electrode, an electrode composed of metallic lithium or one of its alloys, optionally in the form of a nanometric dispersion in lithium oxide, or double nitrides of lithium and of a transition metal, or oxides of low potential having the general formula $Li_{4-x+y}Ti_{5+x}O_{12}$ ($0 \leq x \leq 1$, $0 \leq y \leq 3$), or carbon and carbonaceous products resulting from the pyrolysis of organic materials. The positive electrode will advantageously be chosen from vanadium oxides $VO_x$ ($2 \leq x \leq 2.5$), $LiV_3O_8$ or $Li_yN_{1-x}CO_xO_2$ ($0 \leq x \leq 1$; $0 \leq y \leq 1$), manganese spinels $Li_yMn_{1-x}M_xO_2$ (M=Cr, Al, V, Ni, $0 \leq x \leq 0.5$; $0 \leq y \leq 2$), organic polydisulfides, FeS, $FeS_2$, iron sulfate $Fe_2(SO_4)_3$, iron and lithium phosphates and iron and lithium phosphosilicates with an olivine structure or analogous phosphosilicates in which the iron is replaced by manganese, and sulfophosphates with a Nasicon structure $Li_xFe_2S_{1-x}P_xO_4$. The abovementioned compounds may be used alone or as a mixture.

When an electrolyte according to the present invention is used in a system for modulating light, such as an electrochromic system, use is preferably made of an electrode material chosen from $WO_3$, $MoO_3$, iridium hydroxide oxides $IrO_xH_y$, $2 \leq x \leq 3$; $0 \leq y \leq 3$), Prussian blue, viologen compounds and their polymers, and aromatic polyimides.

When an ionically conducting material of the present invention is used as electrolyte in an energy storage system, such as a supercapacitor, use is preferably made of an electrode material comprising a carbon with a high specific surface or an electrode comprising a redox polymer.

The monomer compounds of the present invention can be used for the doping of polymers for the purpose of conferring an improved electronic conduction on them. The polymers concerned are essentially polyacetylenes, polyphenylenes, polypyrroles, polythiophenes, polyanilines, polyquinolines, which may or may not be substituted, and polymers in which the aromatic units are separated by the vinylene unit —CH=CH—. The doping process consists in partially oxidizing the polymer in order to create carbocations, the charge of which is compensated for by the anions of the compounds of the invention. This doping can be carried out chemically or electrochemically, optionally simultaneously with the formation of the polymer. For this specific application, the choice is preferably made of the compounds of the invention carrying a highly delocalized charge, in particular compounds in which Z is —C(C≡N)$_2$, —NSO$_2$R or —C(SO$_2$R)$_2$, which confer thermal and mechanical stability properties.

The compounds of the present invention can also be used to confer antistatic properties or microwave-absorbing properties on various materials. The materials concerned are, for example, polymers which take part in the composition of electronic components, textiles and windows. Homo- or copolymers of the compounds of the invention, which are preferably non-crosslinked in order to be able to be coated onto the surface on which the antistatic properties have to be induced, are compounds suited to this specific use. The comonomer of this type of application makes possible, if appropriate, a good adhesion to the substrate to be treated, by the choice of comparable polarities. In plastics, it is also possible to prepare mixtures with the polymer of the invention by techniques known in plastics technology.

A copolymer obtained by copolymerization of a mixture of monofunctional compounds and of difunctional compounds according to the present invention is of use in the preparation of membranes. The homopolymerization or the copolymerization of the monomers according to the invention having a perfluorovinyl functional group results in linear polymers. It is easy, by addition of monomers having more than one polymerizable functional group, to obtain crosslinked networks. These materials can be used for preparing membranes having an improved mechanical strength in which the degrees of swelling and the permeation in liquids in which they will be employed can be controlled. The improvement in the mechanical strength is also a significant factor in the preparation of very fine membranes in which the resistance is decreased and in the reduction of the cost of the starting materials. Likewise, controlling the degree of crosslinking makes it possible to increase the concentration of attached ions in the membrane without inducing excessive solubility or excessive swelling. In processes employing membranes, it is particularly advantageous to prepare the membrane in its definitive form, in the sheet or pipe form, from a concentrated solution of monomers in a solvent allowing spreading or extrusion techniques, by copolymerization of the monomers, including those which make possible the crosslinking.

In the preparation of membranes, it is particularly advantageous to use monomer compounds of the present invention which exhibit a high solubility in the solvents in which the polymerization will be carried out and a reactivity comparable with that of the double bonds carried by the monofunctional monomer and of those carried by the polyfunctional monomers which make possible the crosslinking, so as to obtain an even distribution of the crosslinking nodes.

The membranes obtained from the compounds of the present invention can be used in particular in dialysis systems, as separator in a two-phase reactor or for membrane processes of chlorine-sodium hydroxide type, or for the recovery of effluents, or as electrolyte in a fuel cell. As regards fuel cells, a macromolecular material obtained from monomer compounds of the invention can also be used as binder in the electrode material.

The monomer compounds of the present invention can be used for the catalysis of various types of chemical reactions and in particular for polymerization reactions, condensation reactions, addition or elimination reactions, oxidation or reduction reactions, solvolyses, Friedel-Crafts reactions and Diels-Alder reactions. For these applications in catalysis, the monomer compounds will be chosen essentially according to the cation associated with the anionic part. For the catalysis of Diels-Alder reactions or of Friedel—Crafts reactions, alkali metal, alkaline earth metal, transition metal or rare earth metal cations are preferred. It is also possible to use, for the abovementioned catalytic reactions, polymers obtained from the abovementioned monomer compounds. Polyanionic polymers comprising $H^+$, $Li^+$, $Mg^{++}$, $Ca^{++}$, $Cu^{++}$, $Zn^{++}$, $Al^{+++}$ or $Fe^{+++}$ cations or rare earth metal cations are preferred. Said polymers are generally put into the powder or granule form. In this case, the separation of the reactants becomes particularly easy due to the insolubility of the polyanion of the invention.

The compounds of the invention in which the cation is an onium of the diazonium, sulfonium, iodonium or metallocenium type can be used as cationic polymerization initiator. Under the action of actinic radiation, such compounds generate the corresponding acid form capable of initiating a cationic polymerization reaction. It is also possible to use polymers obtained by polymerization of the abovementioned monomer compounds. The advantages related to the use of polymers are analogous to those of the polymers used in the other abovementioned catalytic reactions. The materials of the invention in the amine salt form can be used as initiator of cationic polymerizations by heating, releasing the corresponding protonic form. Likewise, if the cation is a salt of a cationic azo compound (for example as represented below), it can act, by heating, as initiator of radical polymerizations.

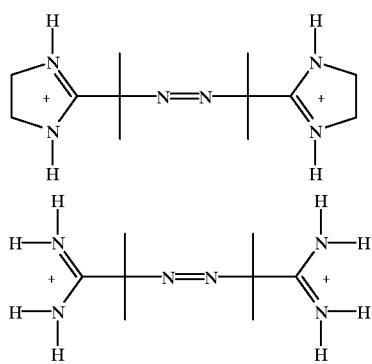

The present invention is described in more detail by the following examples, the invention not being restricted to these examples.

EXAMPLE 1

An azeotropic distillation of 20 mmol of carboxylic acid $ClCF_2CFClCOOH$ and of 10 mmol of hydrazine monohydrate was carried out in 200 ml of toluene. After 24 hours, the toluene was evaporated and the compound $ClCF_2CFClCONHNHCOCFClCF_2Cl$ was obtained. This compound was subsequently dissolved in 200 ml of $PCl_5$ comprising 40 mmol of dimethylaniline hydrochloride. After having brought this mixture to reflux for 24 hours, two phases were obtained after cooling, including a denser $ClCF_2-CFCl-CCl=N-N=CCl-CFCl-CF_2Cl$ phase. This product was recovered using a separating funnel, washed with water and then treated with aqueous ammonia in a mixture of 100 ml of ether and 100 ml of a 4M aqueous ammonia solution. After stirring for 24 hours, the solvents were evaporated and $ClCF_2-CFCl-C(NH_2)=N-N=C(NH_2)CFClCF_2Cl$ was thus obtained. The latter product was subsequently brought to reflux in 100 ml of butanol for 48 hours and then, after the evaporation of butanol, taken up in 100 ml of anhydrous THF comprising zinc. After 24 hours, the solvent was evaporated and the residual product recrystallized from a saturated KCl solution. After filtration, the recrystallized compound was ground up together with ammonium sulfate and then sublimed under vacuum, and the following compound was thus recovered:

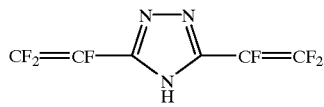

EXAMPLE 2

10 mmol of hydrazine monohydrate were treated in THF with 15 mmol of $CF_3CO_2C_2H_5$. After 8 hours, the THF was evaporated and the product dried. $CF_3CONHNH_2$ was obtained quantitatively. An azeotropic distillation of this compound with 10 mmol of the carboxylic acid $ClCF_2CFClCOOH$ was then carried out in 200 ml of toluene. After 24 hours, the toluene was evaporated and $ClCF_2CFClCONHNHCOCF_3$ was obtained. This compound was subsequently treated by a process analogous to that described in Example 1 for the compound $ClCF_2CFClCONHNHCOCFClCF_2Cl$ and the following compound was obtained:

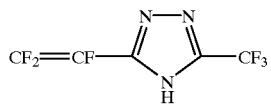

EXAMPLE 3

10 mmol of trifluorovinyl iodide $CF_2=CFI$ were slowly added to 30 ml of anhydrous THF at 0° C. under argon comprising 20 mmol of zinc. After stirring for two hours, the excess zinc was removed by filtration under argon. 5 mmol of the lithium salt of 2,5-dibromo-1,3,4-triazole and 1 mmol of $Pd[P(C_6H_5)_3]_4$ as catalyst were then added to the zincic solution. After stirring for 24 hours, the solvent was evaporated and then the residue was ground up together with ammonium hydrogensulfate. After subliming this mixture, the following compound was obtained:

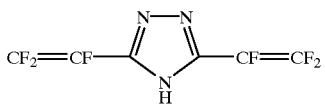

EXAMPLE 4

10 mmol of the lithium salt of urazole and 500 μmol of 1,8-bis(dimethylamino)anthracene were introduced into 50 ml of THF in a chemical reactor. After having brought the reaction mixture to −20° C., 20 mmol of tetrafluoroethylene (PCR) were introduced slowly into the reactor. After 24 hours, the reaction mixture was flushed with argon and then the mixture was allowed to slowly return to room temperature. 30 mmol of sodium tert-butoxide, in solution in 20 ml of anhydrous THF, were then slowly added. After 3 hours, the solvent was evaporated and the residue was recrystallized from a saturated KCl solution and then sublimed, after having been ground up together with ammonium sulfate. The following compound was obtained:

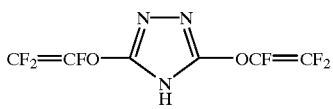

EXAMPLE 5

10 mmol of 1-trifluoromethyl-3-hydroxy-2,4,5-triazole were reacted with 10 mmol of tetrafluoroethylene by a process similar to that described in Example 4. The following compound was thus obtained:

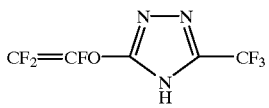

EXAMPLE 6

10 mmol of freshly sublimed malononitrile were dissolved in 50 ml of anhydrous THF and then the solution was brought to 0° C. 20 mmol of lithium hydride LiH were then added portionwise. After 2 hours, 10 mmol of ClCF$_2$CFClSO$_2$F were added. After 48 hours, the solution was centrifuged in order to remove the LiF precipitate and then the solvent was evaporated.

EXAMPLE 7

25.5 g of the acid chloride BrC$_6$H$_4$SO$_2$Cl were suspended in a solution of 5.4 g of ammonium chloride in 100 ml of water maintained at 0° C. and then 108 g of 15% sodium hydroxide solution were gradually added with vigorous stirring, the addition being controlled so that the pH did not exceed 10.5. The stoichiometric ratio of the reactants was 2:1:4. The reaction scheme is:

2BrC$_6$H$_4$SO$_2$Cl+NH$_4$Cl+4NaOH→3NaCl+(BrC$_6$H$_4$SO$_2$)$_2$NNa+4H$_2$O.

The solution was subsequently filtered and then evaporated and the sodium salt of the bis(4-bromobenzenesulfonimide) (BrC$_6$H$_4$SO$_2$)$_2$NNa was extracted with anhydrous ethanol. The salt was recrystallized from a methanol-methyl ethyl ketone mixture.

EXAMPLE 8

24.5 g of 1,1,1,2-tetrafluoroethane were condensed in 300 ml of anhydrous ether at −78° C. 44 ml of a 10M solution of butyllithium in hexane were subsequently added dropwise with stirring. After one hour, 250 ml of a commercial 1M solution of zinc chloride in ether were added to the reaction mixture. The reaction was carried out according to the following reaction scheme:

CF$_3$C$_2$H$_2$F+C$_4$H$_9$Li→C$_4$H$_{10}$+CF$_2$=CFLi+HF

CF$_2$=CFLi+ZnCl$_2$→CF$_2$=CFZnCl+LiCl

The suspension containing the zincic trifluorovinyl was brought back to ordinary temperature and 45 g of the sodium salt of bis(bromophenylsulfonimide) (prepared according to the procedure of Example 7) in 150 ml of anhydrous dimethylformamide were added, as well as 800 mg of trisbenzylideneacetonedipalladium(0) and 1 g of triphenylphosphine. The ether was subsequently removed by distillation while flushing with dry argon and the mixture was maintained at 70° C. for six hours. The reaction product was filtered and the DMF was removed using a rotary evaporator under partial vacuum at 60° C. The solid residue was taken up in 100 ml of water and filtered. The tetraethylammonium salt of the bis(trifluorovinylphenylsulfonimide) was precipitated by addition of 20 g of (C$_2$H$_5$)$_4$NCl in solution in 50 ml of water. The crude product was recrystallized from an ethanol-water mixture. It corresponds to the formula:

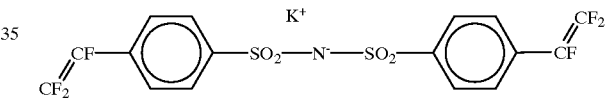

EXAMPLE 9

302 g of iodophenylsulfonyl chloride IC$_6$H$_4$SO$_2$Cl (commercial "pipsyl chloride") were dissolved in 1 l of acetonitrile at 25° C. and 105 g of trifluoromethanesulfonaminde and 225 g of 1,4-diazabicyclo-[2,2,2]-octane (DABCO) were added. The mixture was stirred for 8 hours, during which a DABCO hydrochloride precipitate was formed. The reaction mixture was subsequently filtered and the solvent evaporated. The solid residue was taken up in 300 ml of a saturated potassium chloride solution and 100 ml of acetic acid. The precipitate formed, which corresponds to the formula:

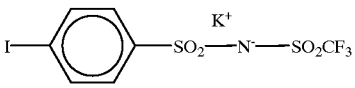

was separated by filtration and recrystallized from water.

362.6 g of the salt thus prepared were dissolved in 700 ml of DMF and 185 g of the zincic derivative in ether prepared by a process similar to that described in Example 8, as well as 2.5 g of trisbenzilidenedipalladium(0) and 4 g of triphenylphosphine, were added. The ether was subsequently distilled off under an argon flow and the mixture was maintained at 60° C. with stirring for 5 hours. The reaction product was filtered and the DMF was removed using a rotary evaporator under partial vacuum at 60° C. The solid residue was washed with water saturated with KCl, dried and then washed with dichloromethane. The salt obtained was purified by crystallization from a water-ethanol mixture. It corresponds to the formula:

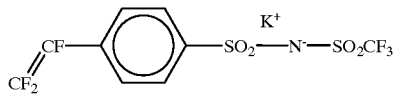

EXAMPLE 10

40 g of the monofunctional ionic monomer prepared according to the procedure described in Example 9 and 2.9 g of the difunctional ionic monomer prepared according to the procedure of Example 8 were dissolved in 100 ml of DMF. 7.5 g of colloidal silica [composed of particles having a mean size of 0.007 microns (Aldrich 38,126–8)] and 600 mg of 1,2-diphenyl-1-keto-2,2-dimethoxyethane

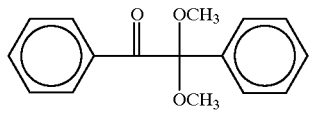

were added to the solution thus obtained. The suspension was homogenized and degassed by sparging with nitrogen, then sprayed as a 60 μm layer over a film of poly(ethylene terephthalate) (PET), and finally subjected for 50 seconds to UV irradiation of 1 W/cm² produced by a lamp of Hanovia type. The film was maintained under a nitrogen blanket during the exposure and the postcure of 5 minutes. The viscous solution solidified to form an elastic film. The DMF was removed by stoving for 48 hours at 80° C., which made it possible to separate the polyelectrolyte membrane from its PET support. The membrane was washed with aqueous acidic solution (1M nitric acid solution) renewed several times. The ions (K+TEA) of the membrane thus obtained were exchanged by protons. The membrane was washed with distilled water and then dried under vacuum to give a rigid film having a thickness of approximately 18 μm and a very good mechanical strength.

EXAMPLE 11

4 g of the monofunctional ionic monomer prepared according to the procedure described in Example 9 and 0.7 g of the difunctional ionic monomer prepared according to the procedure of Example 8 were dissolved in 15 ml of DMF and emulsified by vigorous mechanical stirring in toluene, using 500 mg of Brij 35® as surfactant. After degassing, the polymerization was initiated at 80° C. with 100 mg of benzoyl peroxide and the polymerization was continued for 3 hours at this temperature. The crosslinked suspension of polymer was filtered and then washed with water and with methanol, so as to remove the DMF. After drying, a fine resin powder was obtained. The cations associated with the sulfonimide groups were exchanged for yttrium ions by stirring 2 g of the resin obtained in 6 successive baths of 10 ml of 1M yttrium chloride. The resin was dehydrated. It has catalytic properties, in particular in the Diels-Alder and Friedel-Crafts reactions, in organic solvents. The use of the resin as catalyst is particularly advantageous because of its insolubility, which makes possible separation after the reaction by simple filtration of the reaction mixture.

EXAMPLE 12

46.4 g of commercial 4-hydroxybenzenesulfonic acid sodium salt were dried under vacuum at 60° C. to remove the water of crystallization and then dissolved in 150 ml of anhydrous ethanol, to which were added 14 g of sodium ethoxide and then 28 g of 2-methyl-2-bromopropane. The solution was filtered and the solvent evaporated to dryness. The sodium 4-t-butoxybenzenesulfonate was recrystallized from a mixture of ethanol and ethyl acetate. 21.4 g of (chloromethylene)dimethylammonium chloride [CH(Cl)=N(CH3)$_2$]$^+$Cl$^-$ were added to 42 g of this salt in suspension in 200 ml of anhydrous DMF, the mixture was stirred for 1 hour at 25° C. and then 5.8 g of lithium nitride were added. After reacting for 8 hours, the mixture was filtered and the DMF was removed using a rotary evaporator under partial vacuum at 60° C. The solid residue was taken up in 40 ml of trifluoroacetic acid, which catalyzes the solvolysis reaction of the t-butyl ether. The acid was subsequently distilled off and the mixture was taken up in 80 ml of water with 14 g of potassium carbonate. The residue, after evaporation of the water, was extracted in ethanol and the following salt was obtained:

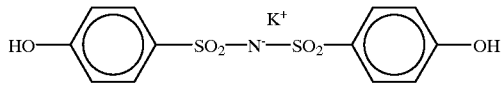

which was recrystallized from this solvent. 22 g of this salt were suspended in 150 ml of THF in a Parr reactor with 1 g of potassium t-butoxide. The reactor was purged under argon and tetrafluoroethylene was introduced under a pressure of 5 bar. After one hour, the pressure fell to 1 atmosphere and the reactor was flushed with argon. The salt obtained, having the formula

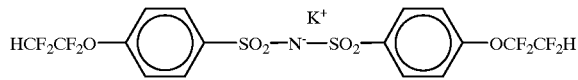

was treated with 13.4 g of potassium t-butoxide in 50 ml of anhydrous THF. The reaction product was filtered and then evaporated. The monomer salt obtained:

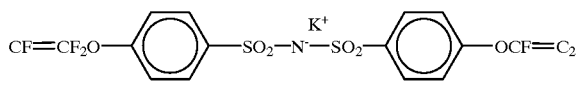

is recrystallized from water.

EXAMPLE 13

18.3 g of the compound

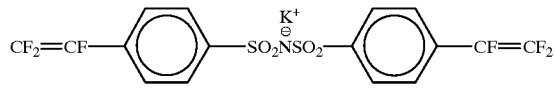

prepared according to the procedure described in Example 12, was suspended in 100 ml of anhydrous DMF in a reactor with 2.6 g of sodium hydride. After cessation of the evolution of hydrogen, 7 g of 1,2-dibromotetrafluoroethane were added. The mixture was stirred at 60° C. for 2 hours. The reaction product was subsequently filtered, the DMF evaporated and the residue taken up in water and filtered. The crystals of $$BrCF_2CF_2O-\underset{}{\bigcirc}-SO_2-\overset{K^+}{N}-SO_2-\underset{}{\bigcirc}-OCF_2CF_2Br$$

were dewatered and dried.

This product was reduced in 150 ml of anhydrous acetonitrile at reflux under argon with 8 g of zinc powder. The resulting solution was filtered, in order to remove the excess zinc, and then evaporated. A salt identical to the preceding example was obtained and recrystallized from an ethanol-water mixture.

$$CF=CF_2O-\underset{}{\bigcirc}-SO_2-\overset{K^+}{N}-SO_2-\underset{}{\bigcirc}-OCF=C_2$$

This monomer easily polymerizes by heating, in particular in concentrated solution, more conveniently in nonvolatile solvents, such as propylene carbonate, to give, at 150° C., a thermostable linear polymer:

$$\left[ -O-\underset{}{\bigcirc}-SO_2-\overset{K^+}{N}-SO_2-\underset{}{\bigcirc}-O-\underset{CF-CF}{\overset{F_2C-CF_2}{|\quad\quad|}}- \right]_n$$

In the presence of a monofunctional comonomer, this monomer behaves as a difunctional monomer, allowing crosslinking.

EXAMPLE 14

100 g of $ClCF_2CFClSO_2F$ were synthesized according to the method described by Forohar Farhad ("Studies of the Chemistry of Perfluorovinylsulfonyl Fluoride", Clemson University, Thesis 1990 UMI 9115049).

10 mmol of freshly sublimed malononitrile were dissolved in 50 ml of anhydrous THF and then the solution was brought to 0° C. 20 mmol of lithium hydride LiH were then added portionwise. After 2 hours, 10 mmol of $ClCF_2CFClSO_2F$ were added. After 48 hours, the solution was centrifuged to remove the LiF precipitate and then 20 mmol of activated zinc were added. After stirring for 24 hours, the THF was evaporated and the residue taken up in acetonitrile and then filtered. After evaporation of the filtered solution and drying, the following compound was obtained:

$$CF_2=CF-SO_2\overset{CN}{\underset{CN}{C^\ominus}}Li^+$$

EXAMPLE 15

10 mmol of trifluorovinyl iodide $CF_2=CFI$ were slowly added to 30 ml of anhydrous THF at 0° C. under argon comprising 20 mmol of zinc. After stirring for two hours, the excess zinc was removed by filtration under argon. 5 mmol of the potassium salt of bis(chlorosulfonyl)imide and 1 mmol of $Pd[P(C_6H_5)_3]_4$, as catalyst, were then added to the zincic solution. After stirring for 24 hours, the solvent was evaporated and then the residue was recrystallized from a saturated potassium chloride solution. After filtering and drying, the following compound was recovered:

$$CF_2=CFSO_2\overset{K}{N}SO_2CF=CF_2$$

The lithium salt was obtained by ionic exchange with lithium chloride in tetrahydrofuran.

What is claimed is:

1. A membrane comprised of a crosslinked copolymer of at least two ionic compounds in which the negative charge is highly delocalized, corresponding to the formula $[CF_2=CF-A^-]_m M^{m+}$ in which:

$M^{m+}$ is a proton or a metal cation having the valency m chosen from the alkali metal, alkaline earth metal, transition metal or rare earth metal ions or an organic onium cation or an organometallic cation, $1 \leq m \leq 3$;

A is an anionic group having one of the formulae (I) $[-(CF_2)_n-SO_2Z]^-$, (II) $[-(O)_{n'}-\Phi-SO_2Z]^-$ or (III)

$$\begin{array}{c} -D \\ | \\ C-X^1 \\ X^4 \diagdown_\ominus \diagup X^2 \\ X^3 \end{array}$$

n and n' represent 0 or 1;

$\Phi$ represents a condensed or noncondensed aromatic group, which may or may not carry one or more substituents and which may or may not comprise heteroatoms, or a polyharlongenated group $-C_6H_{(4-x-y)}F_xCl_y-$ ($1 \leq x+y \leq 4$);

Z represents $-O$ or one of the $-NC\equiv N$, $-C(C\equiv N)_2$, $-NSO_2R$ or $-C[SO_2R]_2$ groups, Z being other than $-O$ when n or n' are zero;

D represents a single bond, an oxygen atom, a sulfur atom, a $-CO-$ carbonyl group or an $-SO_2-$ sulfonyl group;

the groups $X^1$ to $X^4$, hereinafter denoted by $X^i$, represent N, $C-C\equiv N$, CR, CCOR or $CSO_2R$, it being understood that, in a pentacyclic group, the $x^i$ groups can be identical or different;

R represents Y, YO—, YS—, $Y_2N$—, F, $R_F=C_qF_{2q+1}$ (preferably $0 \leq q \leq 12$), $CF_2=CF-$, $CF_2=CFCF_2-$ or $CF_2=CF-O-$, it being understood that, if 2 R substituents are present on the same group, they can be identical or different;

Y represents H or a monovalent organic radical having from 1 to 16 carbon atoms chosen from alkyl, alkenyl, oxaalkyl, oxaalkenyl, azaalkyl, azaalkenyl, aryl or alkylaryl radicals or from the radicals obtained from the abovementioned radicals by substitution, in the chains and/or the aromatic part, by heteroatoms, such as halogens, oxygen, nitrogen, sulfur or phosphorus, it being understood that, if sulfur or phosphorus are present, they can optionally be bonded to substituted nitrogen or oxygen atoms, or else Y is a repeat unit of a polymeric backbone; and at least one of the ionic compounds carries only one $CF_2=CF-$ group and at least one of the ionic compounds carries at least two $CF_2=CF-$ groups.

2. A membrane according to claim 1, characterized in that $M^{m+}$ is a metal cation chosen from the group consisting of $Li^+$, $K^+$, $Mg^{++}$, $Ca^{++}$, $Ba^{++}$, $Cu^{++}$, $Zn^{++}$, $Fe^{++}$ and $Re^{+++}$.

3. A membrane according to claim 1, characterized in that $M^{m+}$ is an ammonium $[N(Y^j)_4]^+$, an amidinium RC[N(Y$^j$)$_2$]$_2$$^+$, a guanidinium C[N(Y$^j$)$_2$]$_3$$^+$, pyridinium [C$_5$N(Y$^j$)$_6$]$^+$, an imidazolium C$_3$N$_2$(Y$^j$)$_5$$^4$, an imidazolinium C$_3$N$_2$(Y$^j$)$_7$$^+$, a triazolium C$_2$N$_3$(Y$^j$)$_4$$^+$, a carbonium C$_5$(Y$^j$)$_5$C$^+$, an NO$^+$ (nitrosyl), NO$_2$$^+$, a sulfonium [S(Y$^j$)$_3$]$^+$, a phosphonium [P(Y$^j$)$_4$]$^+$ or an iodonium [I(Y$^j$)$_2$]$^+$, the Y$^j$ substituents of the same cation, which can be identical or different, representing one of the substituents indicated for Y.

4. A membrane according to claim 1, characterized in that M$^{m+}$ is an organometallic cation chosen from metallocenium; metal cations coordinated by atoms, such as O, S, Se, N, P or As, carried by organic molecules, these cations optionally forming part of a polymeric backbone; or a trialkylsilyl, trialkylgermanyl or trialkylstannyl group.

5. A membrane according to claim 1, characterized in that the M$^+$ cation is the repeat unit of a conjugated polymer in cationic oxidized form.

6. A membrane according to claim 1, characterized in that the divalent radical Φ is a phenyl C$_6$H$_4$ corresponding to the ortho, meta and para positions of substitution or an aromatic group, a phenyl which is substituted and/or comprising condensed nuclei which may or may not comprise heteroatoms.

7. A membrane according to claim 1 wherein the ionic compound which carries only one CF$_2$=CF— group is selected from the group consisting of ([CF$_2$=CF—SO$_2$NCN]$^-$)$_m$M$^{m+}$, ([CF$_2$=CF—SO$_2$C(CN)$_2$]$^-$)$_m$M$^{m+}$, ([CF$_2$=CFCF$_2$—SO$_2$NCN]$^-$)$_m$M$^{m+}$, ([CF$_2$=CFCF$_2$—SO$_2$C(CN)$_2$]$^-$)$_m$M$^{m+}$, ([CF$_2$=CF—ΦSO$_2$NCN]$^-$]$_m$M$^{m+}$, ([CF$_2$=CF—ΦSO$_2$C(CN)$_2$]$^-$)$_m$M$^{m+}$, ([CF$_2$=CF—ΦSO$_2$NSO$_2$CF$_3$]$^-$)$_m$M$^{m+}$,
([CF$_2$=CF—ΦSO$_2$C(SO$_2$CF$_3$)$_2$]$^-$)$_m$M$^{m+}$, ([CF$_2$=CF—ΦSO$_2$CH(SO$_2$CF$_3$)]$^-$)$_m$M$^{m+}$,

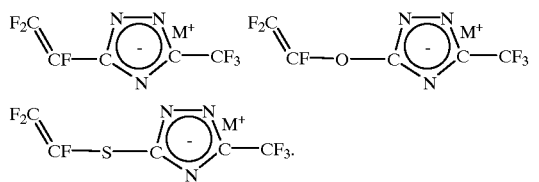

8. A membrane according to claim 1 wherein the ionic compound which carries at least two CF$_2$=CF— groups is selected from the group consisting of
([CF$_2$=CF—SO$_2$)$_2$]$_2$N]$^-$)$_m$M$^{m+}$,
([CF$_2$=CFCF$_2$—SO$_2$)$_2$N]$^-$)$_m$M$^{m+}$,
([(CF$_2$=CFSO$_2$)$_2$CH]$^-$)$_m$M$^{m4}$,
([(CF$_2$=CFCF$_2$—SO$_2$)$_2$CH]$^-$)$_m$M$^{m+}$,
([(CF$_2$=CF—SO$_2$)$_3$C]$^-$)$_m$M$^{m+}$, ([(CF$_2$=CFCF$_2$—SO$_2$)$_3$C]$^-$)$_m$M$^{m+}$,
([(CF$_2$=CF—ΦSO$_2$)$_2$N]—)$_m$M$^{m+}$, ([(CF$_2$=CF—O—ΦSO$_2$)$_2$N])$_m$M$^{m+}$, ([(CF$_2$=CF—ΦSO$_2$)$_2$CH]$^-$)$_m$M$^{m+}$,
([(CF$_2$=CF—O—ΦSO$_2$)$_2$CH]$^-$)$_m$M$^{m+}$, ([(CF$_2$=CF—ΦSO$_2$)$_3$C]$^-$)$_m$M$^{m+}$, ([(CF$_2$=CF—O—ΦSO$_2$)$_2$CH]$^-$)$_m$M$^{m+}$,
([(CF$_2$=CF—ΦSO$_2$)$_3$C]$^-$)$_m$M$^{m+}$,
([(CF$_2$=CFΦSO$_2$)$_2$CH]$^-$)$_m$M$^{m+}$,
([(CF$_2$=CF—O—ΦSO$_2$)$_2$CH]$^-$)$_m$M$^{m+}$, ([(CF$_2$=CF—ΦSO$_2$)$_3$C]$^-$)$_m$M$^{m+}$, ([(CF$_2$=CF—O—ΦSO$_2$)$_2$CH]$^-$)$_m$M$^{m+}$,
([(CF$_2$=CF—ΦSO$_2$)$_3$C]$^-$)$_m$M$^{m+}$,
([(CF$_2$=CF—O—ΦSO$_2$)$_3$C]$^-$)$_m$M$^{m+}$,
([(CF$_2$=CF—)$_2$C$_6$H$_3$SO$_3$]$^-$)$_m$M$^{m+}$,
([3,5-(CF$_2$=CF—)$_2$C$_6$H$_3$SO$_2$NSO$_2$CF$_3$]$^-$)M$^{m+}$

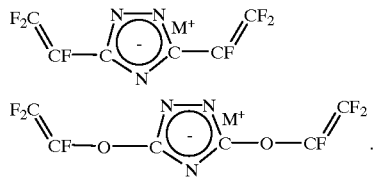

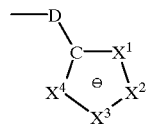

9. A membrane comprised of a crosslinked copolymer of at least two ionic compounds in which the negative charge is highly delocalized, corresponding to the formula [CF$_2$=CF—A$^-$]$_m$M$^{m+}$ in which:

M$^{m+}$ is a proton or a metal cation having the valency m chosen from the alkali metal, alkaline earth metal, transition metal or rare earth metal ions or an organic onium cation or an organometallic cation, 1≦m≦3;

A is an anionic group having one of the formulae (I) [—(CF$_2$)$_n$—SO$_2$Z]$^-$, (II) [—(O)$_{n'}$—Φ—SO$_2$Z]$^-$ or (III)

$$\begin{array}{c} -D \\ | \\ C-X^1 \\ X^4 \diagdown \diagup X^2 \\ X^3 \end{array}$$

n and n' represent 0 or 1;

Φ represents a condensed or noncondensed aromatic group, which may or may not carry one or more substituents and which may or may not comprise heteroatoms, or a polyharlongenated group —C$_6$H$_{(4-x-y)}$F$_x$Cl$_y$— (1≦x+y≦4);

Z represents —O or one of the —NC≡N, —C(C≡N)$_2$, —NSO$_2$R or —C[SO$_2$R]$_2$ groups, Z being other than —O when n or n' are zero;

D represents a single bond, an oxygen atom, a sulfur atom, a —CO— carbonyl group or an —SO$_2$— sulfonyl group;

the groups X$^1$ to X$^4$, hereinafter denoted by X$^i$, represent N, C—C≡N, CR, CCOR or CSO$_2$R, it being understood that, in a pentacyclic group, the x$^i$ groups can be identical or different;

R represents Y, YO—, YS—, Y$_2$N—, F, R$_F$=C$_q$F$_{2q+1}$ (preferably 0≦q≦12), CF$_2$=CF—, CF$_2$=CFCF$_2$— or CF$_2$=CF—O—, it being understood that, if 2 R substituents are present on the same group, they can be identical or different;

Y represents H or a monovalent organic radical having from 1 to 16 carbon atoms chosen from alkyl, alkenyl, oxaalkyl, oxaalkenyl, azaalkyl, azaalkenyl, aryl or alkylaryl radicals or from the radicals obtained from the abovementioned radicals by substitution, in the chains and/or the aromatic part, by heteroatoms, such as halogens, oxygen, nitrogen, sulfur or phosphorus, it being understood that, if sulfur or phosphorus are present, they can optionally be bonded to substituted nitrogen or oxygen atoms, or else Y is a repeat unit of a polymeric backbone; and at least one of the said at least two ionic compounds has all R substituents selected from Y, YO—, YS—, Y$_2$N—, F, or C$_q$F$_{2q+1}$, and at least one of the said at least two ionic compounds has at least one substituent R selected from CF$_2$=CF—, CF$_2$=CFCF$_2$— or CF$_2$=CF—O—.

10. A method for preparing a membrane, comprising the step of copolymerizing at least two ionic compounds in which the negative charge is highly delocalized, corresponding to the formula $[CF_2=CF-A^-]_m M^{m+}$ in which:

$M^{m+}$ is a proton or a metal cation having the valency m chosen from the alkali metal, alkaline earth metal, transition metal or rare earth metal ions or an organic onium cation or an organometallic cation, $1 \leq m \leq 3$;

A is an anionic group having one of the formulae (I) $[-(CF_2)_n-SO_2Z]^-$, (II) $[-(O)_{n'}-\Phi-SO_2Z]^-$ or (III)

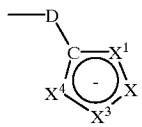

n and n' represent 0 or 1;

$\Phi$ represents a condensed or noncondensed aromatic group, which may or may not carry one or more substituents and which may or may not comprise heteroatoms, or a polyhalogenated group $-C_6H_{(4-x-y)}F_xCl_y-$ ($1 \leq x+y \leq 4$);

Z represents $-O$ or one of the $-NC \equiv N$, $-C(C \equiv N)_2$, $-NSO_2R$ or $-C[SO_2R]_2$ groups, Z being other than $-O$ when n or n' are zero;

D represents a single bond, an oxygen atom, a sulfur atom, a $-CO-$ carbonyl group or an $-SO_2-$ sulfonyl group;

the groups $X^1$ to $X^4$, hereinafter denoted by $X^i$, represent N, $C-C \equiv N$, CR, CCOR or $CSO_2R$, it being understood that, in a pentacyclic group, the $X^i$ groups can be identical or different;

R represents Y, YO—, YS—, $Y_2N$—, F, $R_F=C_qF_{2q+1}$ (preferably $0 \leq q \leq 12$), $CF_2=CF$—, $CF_2=CFCF_2$— or $CF_2=CF-O$—, it being understood that, if 2 R substituents are present on the same group, they can be identical or different;

Y represents H or a monovalent organic radical having from 1 to 16 carbon atoms chosen from alkyl, alkenyl, oxaalkyl, oxaalkenyl, azaalkyl, azaalkenyl, aryl or alkylaryl radicals or from the radicals obtained from the abovementioned radicals by substitution, in the chains and/or the aromatic part, by heteroatoms, such as halogens, oxygen, nitrogen, sulfur or phosphorus, it being understood that, if sulfur or phosphorus are present, they can optionally be bonded to substituted nitrogen or oxygen atoms, or else Y is a repeat unit of a polymeric backbone;

at least one of the ionic compounds carries only one $CF_2=CF-$ group and at least one of the ionic compounds carries at least two $CF_2=CF-$ groups, and forming a membrane with the copolymer.

11. The method according to claim 10, wherein $M^{m+}$ is a metal cation chosen from the group consisting of $Li^+$, $K^+$, $Mg^{++}$, $Ca^{++}$, $Ba^{++}$, $Cu^{++}$, $Zn^{++}$, $Fe^{++}$ and $Re^{+++}$.

* * * * *

UNITED STATES PATENT AND TRADEMARK OFFICE
CERTIFICATE OF CORRECTION

PATENT NO. : 6,288,187 B1
DATED : September 11, 2001
INVENTOR(S) : Armand et al.

It is certified that error appears in the above-identified patent and that said Letters Patent is hereby corrected as shown below:

<u>Title page,</u>
Item [75], add -- Christophe Michot, Grenable (FR) --;

<u>Column 22,</u>
Line 31, "polyharlongenated" should read -- polyhalogenated --;
Line 41, "$x^i$" should read -- $X^i$ --;

<u>Column 23,</u>
Line 2, "$C_3N_2(Y)_5^4$" should read -- $C_3N_2(Y^j)_5^+$ --;
Line 51, "$M^{m4}$" should read -- $M^{m+}$ --;

<u>Column 24,</u>
Line 31, "polyharlongenated" should read -- polyhalogenated --;
Line 42, "$x^i$" should read -- $X^i$ --; and <u>Column 25,</u>
Line 11, the portion of the formula reading
"$C-X^1_{\diagdown X}$" should read -- $C-X^2_{\diagdown X}$ --.

Signed and Sealed this

Eighteenth Day of June, 2002

*Attest:*

JAMES E. ROGAN
*Attesting Officer*    *Director of the United States Patent and Trademark Office*